United States Patent

Bellis, Sr.

[11] Patent Number: 5,996,430
[45] Date of Patent: Dec. 7, 1999

[54] PROBE INSERTION AND RETRACTION ASSEMBLY

[75] Inventor: George Bellis, Sr., Erath, La.

[73] Assignee: Gulf Coast Chemical, Inc., La.

[21] Appl. No.: 09/118,159

[22] Filed: Jul. 16, 1998

[51] Int. Cl.⁶ ............................ G01D 21/00; G01N 1/00; G01L 7/00
[52] U.S. Cl. ....................... 73/866.5; 73/863.86; 73/756
[58] Field of Search ................. 73/756, 863.86, 73/866.5, 863.3, 86; 422/53

[56] References Cited

U.S. PATENT DOCUMENTS

| | | | |
|---|---|---|---|
| 4,120,313 | 10/1978 | Lewis | 422/53 |
| 4,179,920 | 12/1979 | Schuller et al. | 73/86 |
| 4,346,611 | 8/1982 | Welker | 73/863.86 |
| 4,603,113 | 7/1986 | Bauer | 73/86 |
| 4,697,465 | 10/1987 | Evans et al. | 73/866.5 |
| 4,928,536 | 5/1990 | Welker | 73/863.3 |
| 5,106,580 | 4/1992 | Mundiam | 73/866.5 |
| 5,639,975 | 6/1997 | Waterman | 73/866.5 |

*Primary Examiner*—Harshad Patel
*Assistant Examiner*—Robin Clark
*Attorney, Agent, or Firm*—Garvey, Smith, Nehrbass & Doody, LLC

[57] ABSTRACT

A test probe insertion-retrieval tool for pressure vessels and flowlines which includes a generally elongated body, a fixture at one end of the body to secure the body to a pressure vessel or a flowline fitting, including an insulated test probe socket mounted on a rod which passes through the end of the elongated body and guidingly and sealingly through a chamber above the end. There is further provided a piston mounted on the rod in the chamber, allowing a flow of pressurized fluid tapped from the lower chamber through connected tubing to force the piston rod and connected insulated test probe socket into the pressure vessel or flowline. Further, there is provided a system of flow ports for allowing fluid under pressure to flow in relation to the piston so as to allow the piston to return to the up position so that the probe may be removed from the rod for evaluation.

11 Claims, 4 Drawing Sheets

PROBE INSERTION AND RETRACTION ASSEMBLY

BACKGROUND OF THE INVENTION

1. Field of the Invention

The apparatus of the present invention relates to devices for inserting and removing probes from the interior of a pipeline or a vessel while under pressure. More particularly, the present invention relates to an improved corrosion coupon holder for inserting and removing a coupon from the interior of a pipeline or vessel while under pressure through the use of pressurized fluid flow for inserting and retracting the probe from the pipeline or vessel in place of manual manipulation.

2. General Background of the Invention

In the technology of the integrity of pipelines and vessels, there has developed a technique whereby a probe such as a coupon is inserted into the fluid which is contained within the vessel or pipeline, and is kept in place over a period of time, the coupon being of a material which is similar to the material of the interior or pipeline or vessel, so that one may inspect the coupon in order to determine the extent of corrosion that may be taking place within the pipeline or vessel. In the current state of the art, such a coupon is usually inserted into the vessel via a body which is secured to the vessel or pipeline wall and a probe which is mounted on the end of a rod. The rod is then manually inserted through a threadable member or the like into the pipeline or vessel in a sealed condition, so that the fluid within the vessel makes contact with the probe or coupon. In such a device, in the current state of the art, it is often difficult and perhaps unsafe to manually manipulate the probe at the end of the tube member down into the vessel while the vessel is under pressure. Therefore, there is a need in the industry for a coupon or probe holder which can be easily and quickly inserted into the flow space of a flow line or vessel, which is safer and less time consuming.

BRIEF SUMMARY OF THE INVENTION

The apparatus and method of the present invention solves the problem in a simple and straightforward manner. What is provided is a test probe insertion-retrieval tool for pressure vessels and flowlines which includes a generally elongated body, a fixture at one end of the body to secure the body to a pressure vessel or a flowline fitting, including an insulated test probe socket mounted on a rod which passes through the end of the elongated body and guidingly and sealingly through a chamber above the end. There is further provided a piston mounted on the rod in the chamber, allowing a flow of pressurized fluid tapped from the lower chamber through connected tubing to force the piston rod and connected insulated test probe socket to a down position into the pressure vessel or flowline. Further, there is provided a system of flow ports for allowing fluid under pressure to flow in relation to the piston so as to allow the piston to return to the up position so that the probe may be removed from the rod for evaluation.

Therefore, it is a principal object of the present invention to provide an improved probe insertion and retraction assembly which is hydraulically operated for inserting and removing the assembly from the interior of a flowline or vessel;

It is a further object of the present invention to provide an improved probe insertion and retraction assembly which is sealably mountable on the surface of a vessel or flowline and allows an insertion probe such as a coupon to be inserted in the flowline or retrieved from the flowline without the necessity of manual manipulation of the assembly;

It is a further object of the present invention to provide a hydraulically controlled probe insertion and retraction assembly which allows the operator of the assembly to insert and remove the probe from the interior of a flowline or vessel without having to undertake any strenuous, time consuming, or dangerous operation in order to operate the assembly.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
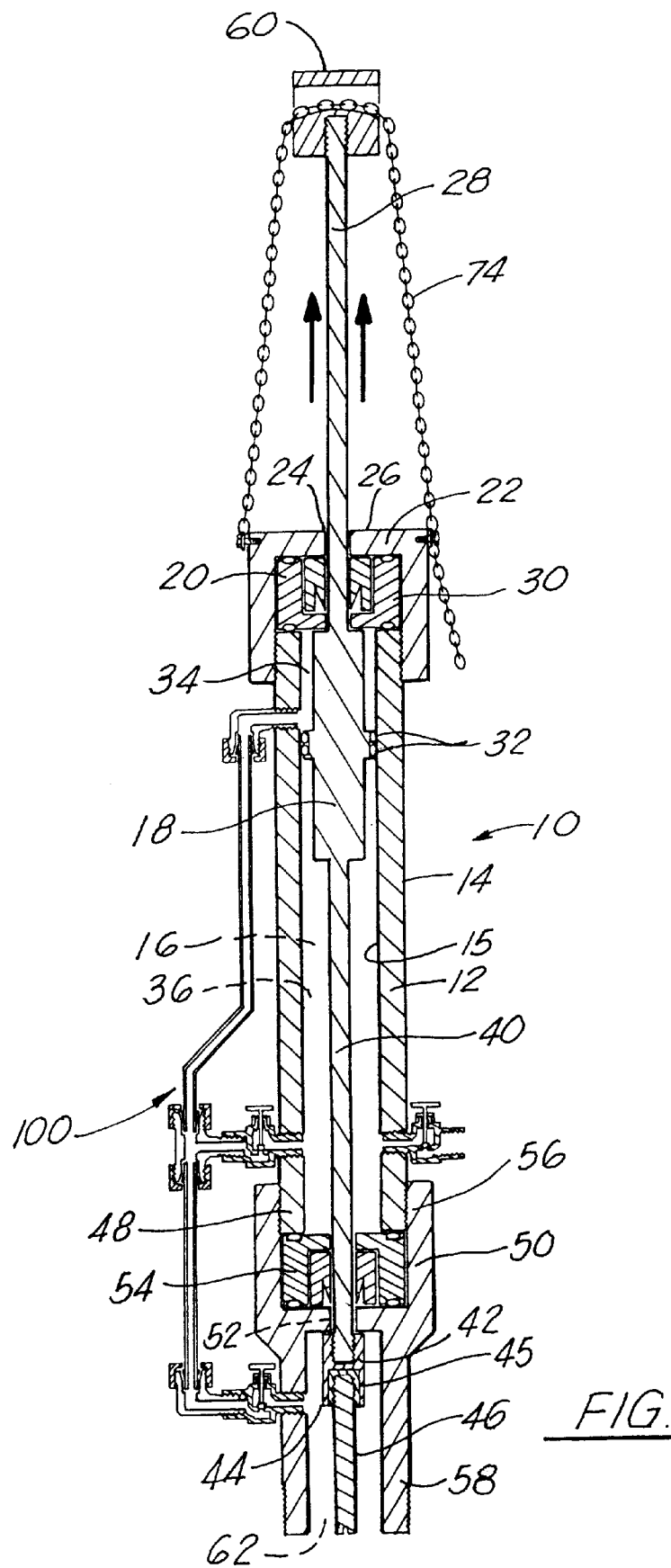
FIG. 1 illustrates the preferred embodiment of the apparatus of the present invention with the assembly not mounted on the vessel or flowline and the probe in the up or retracted position.

FIGS. 1–4 illustrate the preferred embodiment of the apparatus of the present invention by the numeral 10. As illustrated initially in FIG. 1, the improved probe insertion and retraction assembly 10 would comprise principal assembly body 12 having a continuous side wall 14 and defining a space 16 therein for the traveling of the piston member 18 as will be discussed further. The principal body 12 includes an upper threaded end portion 20 which threads into a circular cap portion 22 for sealing off the upper end of the main body 12. Cap 22 further comprises an opening 24 in its top wall 26 for allowing an upper piston rod 28 to travel therethrough with the piston rod 28 terminating on its lower end at the main piston 18 contained within body space 16. As illustrated in FIG. 1, there may be included a packing material 30 between the cap 26 and the upper end 20 of main body 12 so as to seal that space therein.

As further illustrated, the piston 18 includes a pair of O rings 32 which form a fluid seal between the interior wall 15 of body portion 12 and the piston 18, so that fluid does not travel between the upper space 34 above the O rings 32 as the piston 18 moves within space 16 and the lower space 36 beneath the pair of O rings 32. As further illustrated, there is further included a lower piston rod 40 extending from the lower end of main piston 18, the piston rod 40 terminating in a probe holder 42 which is threadably engaged to the lower end of piston rod 40. The holder 42 has a lower end 44 threadably engaged to a probe member 46 such as a coupon or the like type of probe. Lower end 44 includes an insulator 45 which protects the probe against corrosion from the outside. This type of probe is known in the art and is used, as was stated earlier, to be inserted in a flowline or vessel so as to test the rate of any deterioration or corrosion of the wall of the flowline or vessel during use. Again illustrated in FIG. 1, the lower end 48 of main body portion 12, again is threadably engaged to a lower cap portion 50 with lower cap portion 50 including an opening 52 for allowing the lower piston rod 40 to travel therethrough and a packing material 54 to seal off any fluid which is contained within the lower space 36 between the O rings 32 and the lower end 48 of the main body 12. As seen in FIG. 1, the apparatus 10 has a threaded lower end 58 which would be threadably engaged to a lower cap 50 as will be discussed further.

For purposes of operation, it should be noted that the lower cap 50 includes an extended neck portion 58 having an opening 62 to accommodate the probe 46 when the piston 18 has been fully retracted to the up position as seen in FIG. 1. In that Figure, the upper piston rod 28 is extending a distance out of the upper cap 22 and there is an upper member 60 on its uppermost end threadably engaged.

Figure 2:
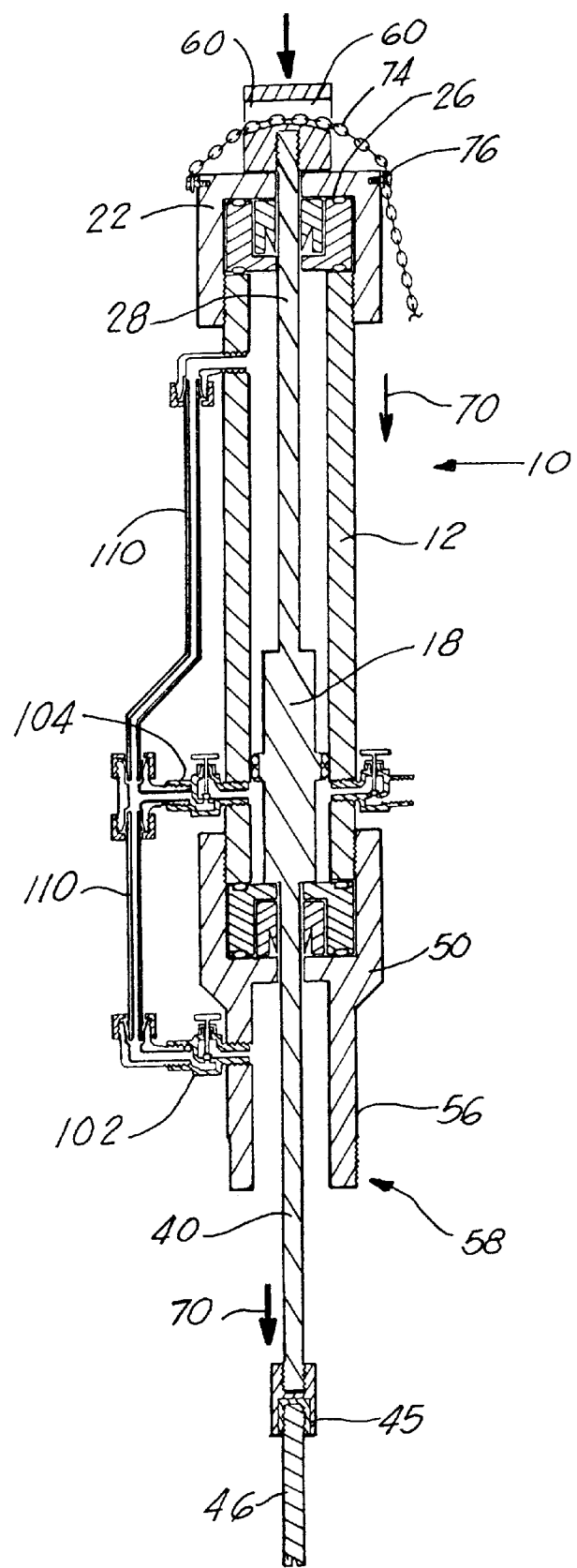
FIG. 2 illustrates the preferred embodiment of the apparatus of the present invention with the assembly not mounted on the vessel or flowline and the probe in the down or insertion position.

There is also illustrated in the Figures a fluid porting system 100 which will be discussed, in relation to the operation of the assembly in later Figures. In regard to FIG. 2, FIG. 2 is an identical cross section view as in FIG. 1, but for the fact that in FIG. 2, the piston 18 has been moved in the direction of arrow 70 to the down position so that the probe 46 is extending out of the neck portion 58. Therefore, when the assembly 10 is threadably engaged to a pipeline or vessel, probe 46 would be within the flow current of the vessel, as will be discussed further. As noted in this position, the top portion 60 of upper rod member 28 is moved to a position up against the upper end 26 of cap 22 as noted. For purposes of safety, there is included as seen in the Figures, an extendable chain 74. Chain 74, for example, as seen in FIG. 1, has been fully extended in order to allow the piston to move to the retracted most position while the probe 46 has been retracted from the flowline or vessel. But, in FIG. 2, when the piston 18 has been moved to the down position, with the probe 46 in the flowline, the chain 74 is moved to its tightened position and hooked in place at point 76. This is to prevent any inadvertent upward movement of the piston 18 by fluid or the like into the position in FIG. 1, which may cause some danger to a worker should the piston 18 be moved swiftly into the fully up position as seen in FIG. 1.

Figure 3:
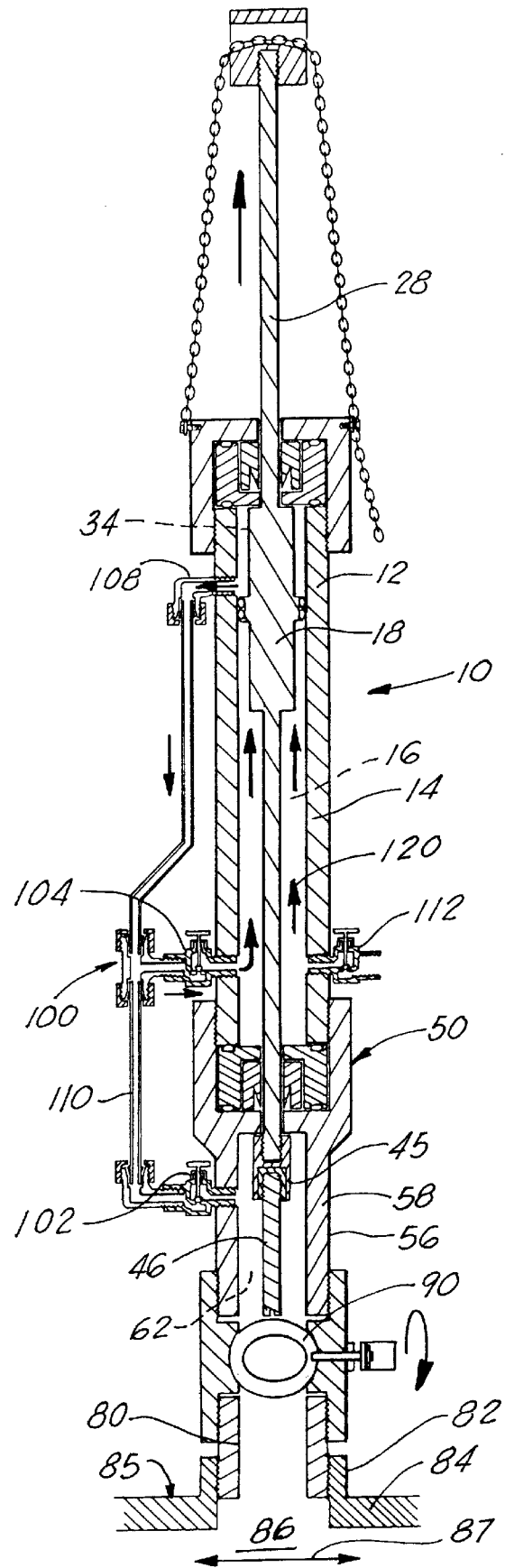
FIG. 3 illustrates the preferred embodiment of the apparatus of the present invention mounted onto a flowline or vessel with the insertion probe in the retracted position prior to the insertion steps.
Figure 4:
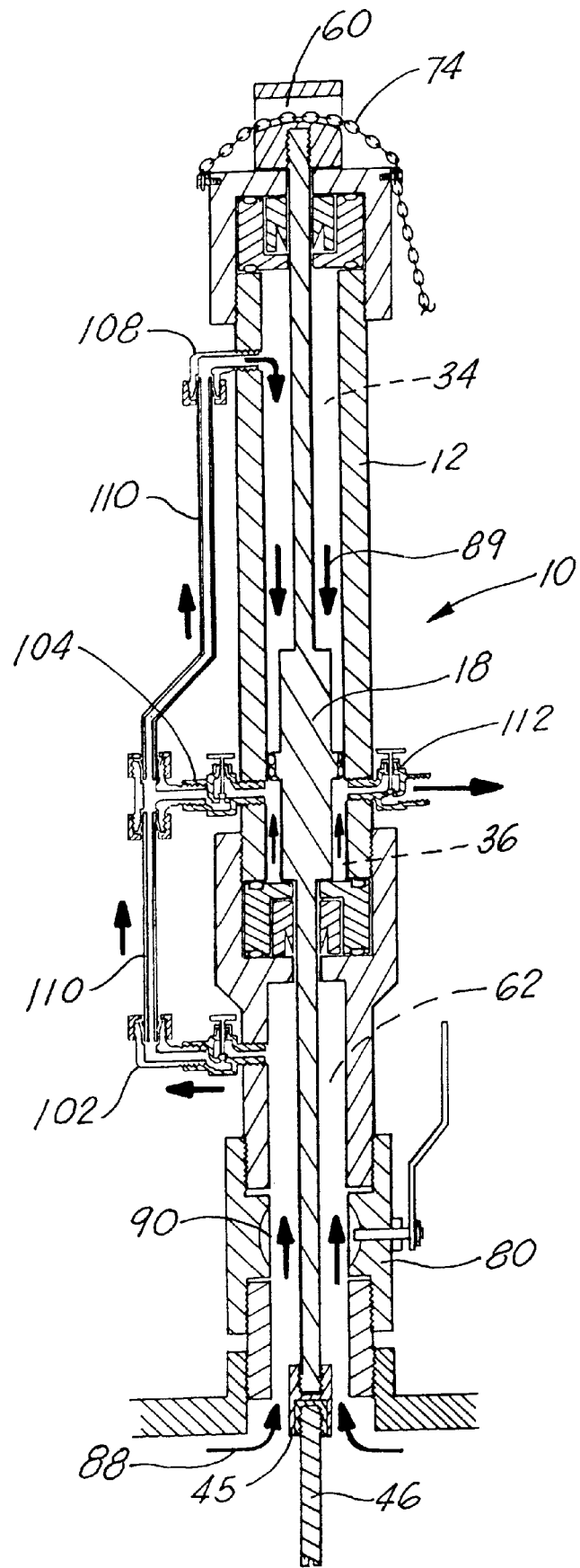
FIG. 4 illustrates the preferred embodiment of the apparatus of the present invention mounted on the wall of a flowline or vessel with the insertion probe in the second inserted position and the coupon or probe within the flowline or vessel space.

Turning now to FIGS. 3 and 4, in these Figures, the assembly 10 again is seen in full cross section view and in FIG. 3, the assembly 10 is illustrated with the piston 18 which has moved to the up position fully so that upper rod 28 is extending the full length out of the body portion 12 and the probe 46 is fully retracted into the opening 62 in neck portion 58 of the lower cap 50. As seen in FIG. 3, the lower end 56 of the cap 50 has been threadably engaged to a valving member 90 which in turn is threadably engaged to a standard NPT nipple 80. The standard NPT nipple 80 would then be threadably engaged to a standard NPT thread-o-let 82 which is formed on the wall 84 of a typical pipeline or vessel 85. The space 86 would represent the space of the vessel where fluid or the like may be flowing, for example, in the direction of arrow 87. As noted, the valving member 90, such as a ball valve, mounted on the standard NPT nipple 80, is fully rotated from a fully closed position as seen in FIG. 3, to a fully open position as seen in FIG. 4, as will be discussed further.

Continuing with FIG. 3, as illustrated in that Figure, as stated earlier the probe 46 has been retracted into the opening 62 and lower neck portion 58 and the valving member 90 has been closed so that no fluid 87 in line 86 can go into the apparatus 10. At this point, the apparatus 10 may be threadably disengaged from the NPT nipple 80, and the probe can be removed from the apparatus for further evaluation.

FIG. 3, the assembly 10 would be threadably engaged to the NPT nipple 80. Once this is accomplished, reference is made to the fluid valving system 100 secured to the outer surface of assembly 10. The fluid valving system 100 would include a first valving member 102 ported into the wall of neck portion 58 and providing access from opening 62 into a flowline 110, which would flow upward to a second valving member 104 which is ported into the principal bore 16 of assembly body 12 and interconnecting flowline 110 which flows further upward to a third ported element 108 which ports into that portion 34 above the piston 18 within body 12. Further, as illustrated, there is a third valving element 112 which is provided in the wall 14 of assembly 12 at substantially the same height as valving element 104, as seen in the Figures.

As seen in FIG. 3 in this position, piston 18 has been fully retracted up into the cylinder, and probe 46 is contained within opening 62 and lower collar 58.

In order to start the procedure, reference is made to FIG. 4 where ball valve 90 is opened, and fluid contained in the vessel 86 flows in the direction of arrow 88 upward into opening 62. At this point, valving element 102 is opened slightly and fluid is allowed to travel upward through line 110, bypass closed valve 104 and upward into flow element 108. Fluid would then continue to flow in space 34 and the pressure of the fluid would push the piston 18 downward in the direction of arrows 89 to its lowermost position, as seen in FIG. 4. At this point, it should be noted that the probe 46 is now moved into the pipeline or vessel 86 in the proper position for testing. When the insertion is achieved as seen in FIG. 4, the valve 102 will be closed completely and the chain 74 will be secured in the manner as seen in FIG. 4, so that no inadvertent upward movement of the upper piston member 28 can occur. Slowly, valve 104 will be opened so as to equalize the pressure above and below piston 18 allowing the force of the pressure area to rest against the chain 74. At this point, the insertion member 46 will remain within flow space 86 of the vessel 85 until it is ready to be retrieved.

Returning now to FIGS. 3 and 4, when the probe 46 is ready to be retrieved, valve 104 will be closed and valve 102 will be slowly opened until slack is apparent in chain 74. When the slack is achieved, valve 102 is closed completely, the chain is unsecured, and slowly valve 104 is opened. When pressure is equalized between spaces 34 and 16, pressure/force from the flowline or vessel pushes rod 40 to the up position as seen in FIG. 3. When the piston 18 is fully in the up position, the valve 90 will then be closed while valves 104 and 112 remain opened so that the tap pressure can be bled through valve 102 passing through valve 104 and 112. When this has occurred, and pressure has been bled off, the assembly 10 can then be threadably disengaged from the NPT nipple and the probe 46 can be removed for further evaluation.

The foregoing embodiments are presented by way of example only; the scope of the present invention is to be limited only by the following claims.

I claim:

1. An improved high pressure test coupon insertion and removal assembly for pressure vessels and flowlines, comprising:

a. a principal generally elongated body portion, having a fluid chamber therein;

b. a lower chamber at one end of said principal body portion to secure said body portion to a pressure vessel or flowline fitting;

c. a rod extending through a top portion of the principal body portion, and into the lower chamber, the rod including a piston means sealably moveable within the fluid chamber;

d. a test coupon mounted on a lower end of the rod below the piston, and extending through the lower end of the body portion into the lower chamber;

e. the test coupon moveable to a down position making contact with fluid within the vessel or flowline, and retractable into the lower chamber for inspection or removal;

f. means for introducing fluid under pressure into the fluid chamber, for forcing the piston to move between a first down position where the test coupon is inserted into the vessel or flowline to the retracted position where the coupon is retracted into the lower chamber; and g. chain means on the outer portion of the apparatus, for securing the rod either in an extended or a retracted position during operation of the apparatus.

2. The apparatus in claim 1, wherein the apparatus is engaged to a valving element between the lower chamber of the apparatus and the vessel or flowline for sealing off the lower chamber when the coupon is to be replaced.

3. The apparatus in claim 1, wherein the means for introducing fluid under pressure to provide upward and downward movement to the piston further comprises a fluid flow line with associated valving members for routing fluid under pressure to either an upper wall or lower wall of the piston, for imparting movement to the piston member within the fluid chamber.

4. The apparatus in claim 1, further comprising a socket member at the lower end of the rod within the chamber for engaging the test coupon thereupon, and providing easy removal of the coupon when it is retracted into the lower chamber.

5. A high pressure test coupon insertion-retrieval apparatus for pressure vessels and flowlines, comprising:

a. an elongated principal body portion, having a top portion, and having a fluid chamber therein;

b. a lower chamber secured to a lower end of said principal body portion for securing the apparatus to a pressure vessel or flowline fitting;

c. a rod extending through the top portion of the principal body portion, and into the lower chamber, the rod including a piston means sealably moveable within the fluid chamber;

d. a test coupon removably mounted on a lower end of the rod below the piston, and extending through the lower end of the body portion into the lower chamber;

e. means for introducing fluid under pressure into the fluid chamber above the piston, for forcing the piston to move to a first down position in the fluid chamber where the test probe is inserted into the vessel or flowline, and for introducing fluid under pressure into the fluid chamber below the piston for forcing the piston to move to a second up position where the coupon is retracted into the lower chamber and out of the flowline or vessel; and f. a chain on the outer portion of the apparatus, for securing the rod either in an extended or a retracted position during operation of the apparatus.

6. The apparatus in claim 5, further comprising a ball valve between the lower chamber and the vessel or flowline for sealing off the lower chamber when the coupon is to be replaced, and for allowing the coupon to be inserted into the flowline or vessel when the ball valve is open.

7. The apparatus in claim 5, wherein there is further provided a test coupon socket which further comprises an insulator which insulates the coupon member against corrosion.

8. The apparatus in claim 5, wherein the means for introducing fluid under pressure to provide upward and downward movement to the piston further comprises a fluid flow line with associated valving members for routing fluid flowing from the flowline or vessel under pressure to flow through an exterior flowline into either the space above the piston, or the space below the piston, for imparting upward or downward movement to the piston within the fluid chamber as required.

9. The apparatus in claim 5, further comprising a socket member at the lower end of the rod within the chamber for engaging the test coupon thereupon, and providing easy removal of the coupon when it is retracted into the lower chamber.

10. A method of providing a test coupon within a vessel or chamber comprising the following steps:

a. providing an apparatus having a principal body portion with a fluid chamber therein, with the fluid chamber housing an elongated rod extending through the lower end of the body portion and having a piston member sealably movable within the chamber;

b. mounting the elongated chamber to the vessel or flowline;

c. providing a coupon on the lower end of the rod for making communication with the fluid within the flowline or vessel;

d. routing a portion of the fluid within the flowline or vessel to a point above the piston within the fluid chamber for forcing the piston to a first down position so that the coupon at the end of the rod is lowered into the fluid of the vessel or chamber; and e. rerouting a portion of the fluid within the vessel or chamber so that the rerouted fluid forces the piston to move to a second up position retracting the coupon from the fluid in the flowline or vessel into a portion of the fluid chamber; and f. providing a means on the outer portion of the apparatus, for securing the rod either in an extended or a retracted position during operation of the apparatus.

11. The method in claim 10 further comprising the step of providing a valving element between the principal body portion and the fluid flowline or vessel for sealing off the fluid communication between the principal body portion and the vessel so that the coupon may be removed for testing or inspection.

* * * * *